(12) United States Patent
Arnold et al.

(10) Patent No.: US 8,101,589 B2
(45) Date of Patent: Jan. 24, 2012

(54) NITRIC OXIDE-RELEASING MOLECULES

(75) Inventors: Ernst V. Arnold, Hagerstown, MD (US); Blaine G. Doletski, Baltimore, MD (US); Robert E. Raulli, Manassas, VA (US)

(73) Assignee: Noxilizer, Inc., Baltimore, MD (US)

( * ) Notice: Subject to any disclaimer, the term of this patent is extended or adjusted under 35 U.S.C. 154(b) by 0 days.

(21) Appl. No.: 12/497,113

(22) Filed: Jul. 2, 2009

(65) Prior Publication Data

US 2009/0270509 A1 Oct. 29, 2009

Related U.S. Application Data

(62) Division of application No. 11/052,745, filed as application No. PCT/US2005/000175 on Jan. 6, 2005, now Pat. No. 7,569,559.

(60) Provisional application No. 60/542,298, filed on Feb. 9, 2004.

(51) Int. Cl.
*A61K 31/655* (2006.01)
*C07C 245/00* (2006.01)

(52) U.S. Cl. .................. 514/149; 534/556

(58) Field of Classification Search .............. None
See application file for complete search history.

(56) References Cited

U.S. PATENT DOCUMENTS

| | | | |
|---|---|---|---|
| 5,212,204 A | 5/1993 | Keefer et al. | |
| 5,519,020 A | 5/1996 | Smith et al. | |
| 5,632,981 A | 5/1997 | Saavedra et al. | |
| 5,650,442 A | 7/1997 | Mitchell et al. | |
| 5,665,077 A | 9/1997 | Rosen et al. | |
| 5,683,668 A | 11/1997 | Hrabie et al. | |
| 5,691,423 A | 11/1997 | Smith et al. | |
| 5,698,738 A | 12/1997 | Garfiled et al. | |
| 5,718,892 A | 2/1998 | Keefer et al. | |
| 5,840,759 A | 11/1998 | Mitchell et al. | |
| 5,910,316 A | 6/1999 | Keefer et al. | |
| 5,962,520 A | 10/1999 | Smith et al. | |
| 6,200,558 B1 | 3/2001 | Saavedra et al. | |
| 6,218,016 B1 | 4/2001 | Tedeschi et al. | |
| 6,232,336 B1 | 5/2001 | Hrabie et al. | |
| 6,270,779 B1 | 8/2001 | Fitzhugh et al. | |
| 6,290,981 B1 | 9/2001 | Keefer et al. | |
| 6,359,167 B2 * | 3/2002 | Toone et al. ........... | 560/147 |
| 6,379,660 B1 | 4/2002 | Saavedra et al. | |
| 6,610,660 B1 | 8/2003 | Saavedra | |
| 6,673,338 B1 | 1/2004 | Arnold et al. | |
| 6,703,046 B2 * | 3/2004 | Fitzhugh et al. ........ | 424/484 |
| 6,855,366 B2 * | 2/2005 | Smith et al. ........... | 427/2.1 |
| 7,105,502 B2 * | 9/2006 | Arnold et al. .......... | 514/149 |
| 7,122,529 B2 | 10/2006 | Ruane et al. | |
| 7,348,319 B2 * | 3/2008 | Hrabie et al. .......... | 514/149 |
| 7,425,218 B2 * | 9/2008 | Keefer et al. .......... | 623/1.16 |
| 7,569,559 B2 * | 8/2009 | Arnold et al. .......... | 514/149 |
| 2007/0196327 A1 * | 8/2007 | Kalivretenos et al. ..... | 424/78.18 |
| 2007/0286840 A1 * | 12/2007 | Arnold et al. .......... | 424/78.35 |
| 2007/0292471 A1 * | 12/2007 | Hrabie et al. .......... | 424/423 |

FOREIGN PATENT DOCUMENTS

| WO | 96/36326 | 11/1996 |
|---|---|---|
| WO | 98/13358 | 4/1998 |

OTHER PUBLICATIONS

Arnold, Ernst V. et al., "Reaction of Nitric Oxide with Benzyl Cyanide to Yield a Bis-Diazeniumdiolated Imidate", Tetrahredron Letters, 41(44), 8421-8424, 2000.*
Bhat et al., "N-Nitroso-N, O-dialkylhydroxylamines: preparation, structure, and mechanism of the hydronium ion catalysed solvolytic nitrous oxide extrusion reaction," J. Chem. Soc., Perkin trans. 2, 2000, vol. 7, pp. 1435-1446.
PCT/US05/00175 International Search Report dated Nov. 4, 2005.
Garry J. Southan et al., "Nitrogen Oxides and Hydroxyguanidines: Formation of Donors of Nitric and Nitrous Oxides and Possible Relevance to Nitrous Oxide Formation by Nitric Oxide Synthase," 1998, Biology and Chemistry, vol. 2 No. 4, pp. 270-286.
Supplementary European Search Report No. 05 70 4997 dated Aug. 10, 2009.
N-Nitroso-N, O-dialkylhydroxylamines: preparation, structure, and mechanism of the hydroinium ion catalysed solvolytic nitrous oxide extrusion reaction; J. Ishwara Bhat, et al., J. Chem. Socl, Perkin Trans. 2, 2000, pp. 1435-1446.
Reaction of nitric oxide with benzyl cyanide to yield a bis-diazeniumdiolated imidate; Ernst V. Arnold, et al., Tetrahedron Letters 41 (2000), pp. 8421-8423.
Office Action issued in Japanese Patent Application No. 2006-553122, mailed Mar. 1, 2011, pp. 1-5.

* cited by examiner

*Primary Examiner* — Fiona T Powers
(74) *Attorney, Agent, or Firm* — Pillsbury Winthrop Shaw Pittman LLP

(57) ABSTRACT

This invention relates to compositions comprising carbon-based diazeniumdiolates that release nitric oxide (NO). The carbon-based diazeniumdiolated molecules release NO spontaneously under physiological conditions without subsequent nitrosamine formation. The present invention also relates to methods of preparing the carbon-based diazeniumdiolated molecules, compositions comprising such molecules, methods of using such compositions, and devices employing such molecule compositions.

8 Claims, 1 Drawing Sheet

NITRIC OXIDE-RELEASING MOLECULES

CROSS-REFERENCE TO RELATED APPLICATIONS

Figure 1:
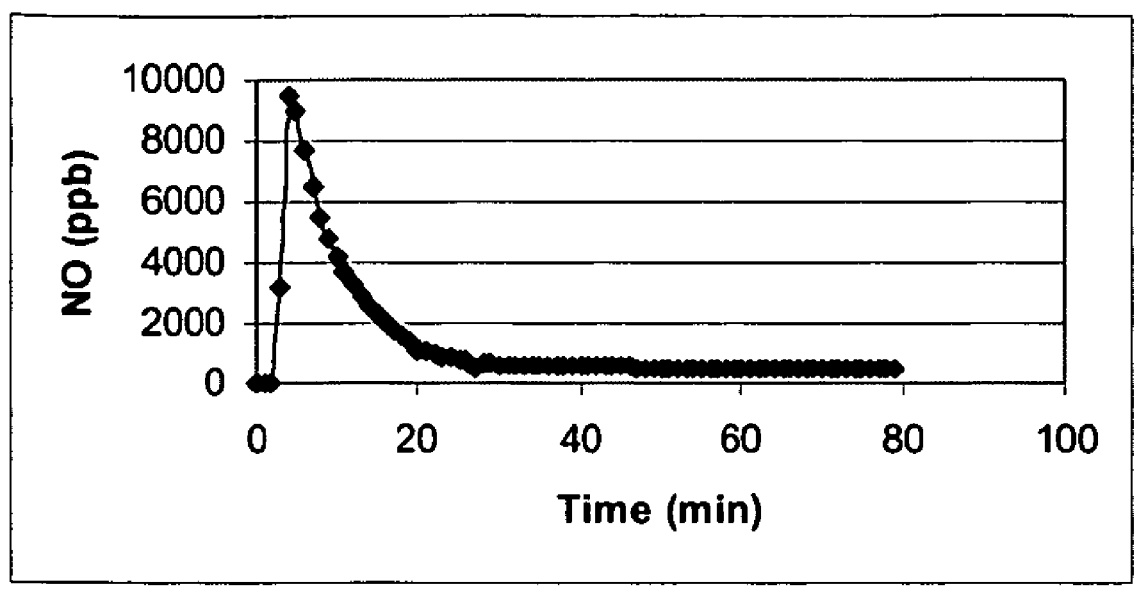

This application claims priority under 35 U.S.C. §120 to U.S. Provisional Application No. 60/542,298 filed Feb. 9, 2004; to PCT/US05/00175 filed Jan. 6, 2005, and to U.S. application Ser. No. 11/052,745, filed Feb. 9, 2005, issued as U.S. Pat. No. 7,569,559; each of which is incorporated herein by reference in its entirety.

STATEMENT OF FEDERALLY-SPONSORED RESEARCH

This work was sponsored by U.S. Public Health Service Grant No. R44 HL062729 from the National Heart Lung and Blood Institute of The National Institutes of Health.

BACKGROUND

1. Field of the Invention

The present invention relates generally to nitric oxide-releasing molecules. More specifically, the present invention relates to carbon-based diazeniumdiolate nitric oxide-releasing molecules.

2. Background of the Invention

Nitric oxide (NO) is a bioregulatory molecule with diverse functional roles in cardiovascular homeostasis, neurotransmission and immune response (Moncada et al., 1990; Marletta et al., 1990). Because NO influences such a vast array of physiological activity, it is desirable to have compounds release NO for use as drugs and physiological and pharmacological research tools. Even more desirable are non-toxic, non-carcinogenic compounds that can generate NO under physiological conditions for therapeutic and clinical applications. Such compounds, however, have been difficult to develop.

Small molecules (generally described as molecules with Formula Weights less than 600) that release NO are well known, and some classes such as the organic nitrates have been used for decades therapeutically.

Diazeniumdiolates are a class of compounds which contain the —[N(O)NO]— functional group and have been known for over 100 years (Traube, 1898). Molecules that bear the diazeniumdiolate group have been disclosed as NO-releasing agents (U.S. Pat. Nos. 4,954,526; 5,039,705; 5,155,137; and 5,208,233). Here the diazeniumdiolate is attached to a primary amine, secondary amine or a polyamine and spontaneously produce nitric oxide under physiological conditions. An advantage to these NO-releasing agents is their wide range of half-lives depending upon the structure of the amine bearing the diazeniumdiolate group (Keefer et al., 1996). The major disadvantage associated with these nitrogen-based diazeniumdiolates is the potential formation of carcinogens (nitrosamines) upon decomposition and release of NO as shown in Equation 1 (Parzuchowski et al., 2002). Some nitrosamines are highly carcinogenic and the potential for nitrosamine formation limits the N-based diazeniumdiolate class of NO donors from consideration as therapeutic agents based on safety issues.

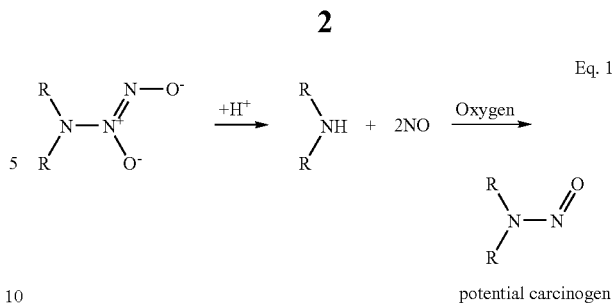

Eq. 1 potential carcinogen

Other non-diazeniumdiolate forms of NO donors have been described including S-nitroso compounds (U.S. Pat. Nos. 5,536,723, Loscalzo et al. and 5,574,068, Stamler et al.) and C-nitroso compounds (U.S. Pat. No. 6,359,182, Stamler et al.). Regarding the S-nitroso compounds, their therapeutic potential is limited due to their rapid and unpredictable decomposition (release of NO) in the presence of trace levels of Cu(I) and possibly Cu(II) ions (Dicks et al., 1996; Al-Sa'doni et al., 1997). Furthermore, S-nitroso compounds may decompose by direct transfer of NO to reduced tissue thiols (Meyer et al., 1994; Liu et al., 1998). Finally, many mammalian enzymes may catalyze the release of NO from S-nitroso compounds (Jourd"heuil et al, 1999a; Jourd"heuil et al., 1999b; Askew et al., 1995; Gordge et al., 1996; Freedman et al., 1995; Zai et al., 1999; Trujillo et al., 1998). However it is well known that tissue and blood levels of ions, enzymes, and thiols are subject to a wide range of variability in each individual, thus making the release of NO unpredictable from subject to subject. The dependence and sensitivity of NO release on blood and tissue components limits the therapeutic potential of nitroso compounds in medicine.

Several references to carbon- or C-based diazeniumdiolate molecules which release NO have been disclosed (U.S. Pat. Nos. 6,232,336; 6,511,991; 6,673,338; Arnold et al. 2000; Arnold et al. 2002; Arnold et al. 2002). C-based diazeniumdiolates are desirable because in contrast to N-based diazeniumdiolates they are structurally unable to form nitrosamines while maintaining their ability to spontaneously release NO under physiological conditions. Hrabie et al. describe a series of enamine-derived diazeniumdiolates of which only one spontaneously releases a small amount of NO (approximately 7% of the theoretical maximum) under physiological conditions (Hrabie et al., 2000; U.S. Pat. No. 6,232,336).

Furthermore, there have been recently published reports on NO-releasing imidates, methanetrisdiazeniumdiolate, and a bisdiazeniumdiolate derived from 1,4-benzoquinone dioxime (Arnold et al. 2000; Arnold et al. 2002a; Arnold et al. 2002b). However the dioxime, which had a favorable NO-release profile of 2 moles of NO per mole of compound, breaks down to a carcinogen (Westmoreland et al., 1992). The methanetris compound is explosive (Arnold et al., 2002) and the imidate class of compounds can cross-link proteins (discussed in detail below).

Arnold et al. disclose NO-releasing imidates and thioimidates of the following general structure (I) (U.S. Pat. No. 6,673,338):

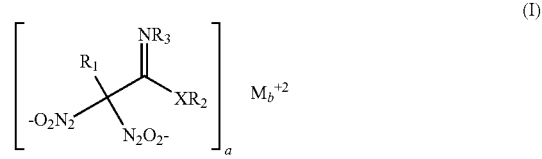

(I)

They also disclose embodiments where the imidate functional group is used to covalently bind the molecule to polymers or biopolymers (proteins), as the imidate functional group is commonly used to bind and/or cross-link proteins (Sekhar et al., 1991; Ahmadi and Speakman, 1978). However the protein binding properties of imidates may be undesirable in applications involving contact with blood, plasma, cells, or tissue because the imidate may react with tissue protein.

Thus there continues to be a need for NO-releasing molecules that release NO spontaneously under physiological conditions and in predictable and tunable quantities of NO, where the NO release is not affected by metals, thiols, enzymes, or other tissue factors that may result in variable NO release, and where the molecule cannot decompose to form nitrosamines and does not covalently bind proteins.

Therefore, it is an object of the present invention to provide a composition that includes a C-based diazeniumdiolate that can generate fluxes of NO spontaneously under physiological conditions. It is a further object of the present invention to provide NO-releasing molecules that generate predictable and tunable NO release rates. It is a further object of the present invention to provide diazeniumdiolate molecules that do not decompose into nitrosamines or covalently bind proteins.

In addition, it is an object of the present invention to provide a method of synthesis for the C-based diazeniumdiolates molecule. A further object of the present invention is to provide methods of use for the C-based diazeniumdiolate molecules in biology and medicine. Further objects and advantages of the invention will become apparent from the following descriptions.

BRIEF SUMMARY OF THE INVENTION

The present invention accomplishes the above-described objects by providing a molecule composition that spontaneously releases NO under physiological conditions, without the possibility to form nitrosamines. The present invention provides a composition for the generation of NO from a C-based diazeniumdiolate that is covalently attached to a phenyl-containing molecule. The present inventors have developed an alternative means of introducing the —[N(O)NO]$^-$ functional group into the molecular backbone by attachment of the —[N(O)NO]$^-$ group to the molecule via a carbon atom, with the general formula:

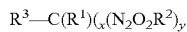    FORMULA 1 where y may be 1-3 and x may be 0-2 wherein the sum of x plus y equals 3, and where $R^1$ is not an amidine, enamine, imidate or thioimidate. $R^1$ may be represented by, but is not limited to an electron withdrawing group such as, but not limited to, a nitro group; an ether group, such as, but not limited to —OCH$_3$, —OC$_2$H$_5$, and —OSi(CH$_3$)$_3$; a tertiary amine; or a thioether, such as, but not limited to, —SC$_2$H$_5$, and -SPh (substituted or unsubstituted). The $R^1$ group may also be a amine, such as, but not limited to, —N(C$_2$H$_5$)$_2$. $R^2$ is a countercation or organic group and $R^3$ is a substituted or unsubstituted phenyl group. The phenyl group may be substituted or unsubstituted as shown in Formula 2 where $R^4$ may be a proton or substitutions on the ring. Manipulation of the $R^1$ group in Formula 1 and 2 can alter the release kinetics and the amount of NO released. Alterations of the $R^1$ group to alter the quantity and kinetics of NO-released is described below.

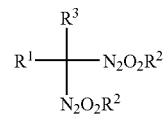    FORMULA 2

DETAILED DESCRIPTION OF THE INVENTION

The present invention provides for a novel class of molecules that contain the —[N(O)NO]$^-$ functional group bound to a carbon atom. The C-based diazeniumdiolates of the present invention are useful for a number of reasons. For example, C-based diazeniumdiolates are advantageous as pharmacological agents, research tools, or as part of a medical device due to their ability to release pharmacologically relevant levels of nitric oxide under physiological conditions without the possibility of forming potent nitrosamine carcinogens. The C-based diazeniumdiolates of the present invention are soluble in aqueous solution.

In Formulas 1 and 2, $R^1$ may not be represented by an amidine, enamine, imidate or thioimidate, or groups which would result in their formation when introducing the diazeniumdiolate functional group. $R^1$ may be represented by the following non-limiting examples: an electron withdrawing group such as but not limited to a nitro group, an ether group, such as, but not limited to —OCH$_3$, —OC$_2$H$_5$, and —OSi(CH$_3$)$_3$; a tertiary amine; or a thioether, such as, but not limited to, —SC$_2$H$_5$, and -SPh (substituted and unsubstituted). The $R^1$ group may also be a amine, such as, but not limited to, —N(C$_2$H$_5$)$_2$.

The $R^2$ group in Formulas 1 and 2 may be a countercation or a covalently bound protecting group. In embodiments where the $R^2$ group is a countercation, the $R^2$ group may be any countercation, pharmaceutically acceptable or not, including but not limited to alkali metals such as sodium, potassium, lithium; group IIa metals such as calcium and magnesium; transition metals such as iron, copper, and zinc, as well as the other Group Ib elements such as silver and gold. Other pharmaceutically acceptable countercations that may be used include but are not limited to ammonium, other quaternary amines such as but not limited to choline, benzalkonium ion derivatives. As understood by those skilled in the art, the negatively charged diazeniumdiolate group must be counterbalanced with equivalent positive charge. Thus, referring to Formula 1, the valence number of the countercation or countercations ($R^2$) must match the stoichiometric number of diazeniumdiolate groups, both represented by y. In embodiments where more than one diazeniumdiolate is bound to the benzylic carbon, and $R^2$ is monovalent, $R^2$ can be the same cation or different cations.

$R^2$ can be any inorganic or organic group covalently bound to the O$^2$— oxygen of the diazeniumdiolate functional group including but not limited to substituted or unsubstituted aryl and glycosyl groups (U.S. Pat. No. 6,610,660, Saavedra et al.), as well as a sulfonyl, acyl, alkyl or olefinic group. The alkyl and olefinic group can be a straight chain, branched chain or substituted chain.

$R^2$ may be a saturated alkyl, such as methyl or ethyl or an unsaturated alkyl (such as allyl or vinyl). Vinyl protected diazeniumdiolates are known to be metabolically activated by cytochrome P-450. $R^2$ may be a functionalized alkyl, such as, but not limited to, 2-bromoethyl, 2-hydroxypropyl, 2-hydroxyethyl or S-acetyl-2-mercaptoethyl. The latter example is an esterase sensitive protecting group. The former examples provide a chemical functional group handle. Such strategies have been successfully employed to link peptides to the diazeniumdiolate molecule. Hydrolysis may be prolonged by addition of the methoxymethyl protecting group. $R^2$ may be an aryl group, such as 2,4-dinitrophenyl. This type of protecting group is sensitive towards nucleophiles, such as glutathione and other thiols. It is obvious to those skilled in the art that several different protecting groups may be used, and/or the stoichiometry of the protecting group addition may be adjusted such that not all the diazeniumdiolate moieties are protected with the same protecting group, or not all the diazeniumdiolate groups are protected at all. By using different protecting groups, or varying the stoichiometry of the protecting group(s) to diazeniumdiolate ratio, the practitioner may engineer the release of NO to a desired rate.

The $R^3$ group in Formulas 1 and 2 is a substituted or unsubstituted phenyl group. The substituents on the phenyl group of Formula 1 and Formula 2 may be any moiety that does not inhibit the NO-releasing properties of the compound and maintains a covalent bond to the molecule backbone. Appropriate moieties include, but are not limited to, aliphatic, aromatic and non-aromatic cyclic groups. Aliphatic moieties are comprised of carbon and hydrogen but may also contain a halogen, nitrogen, oxygen, sulfur, or phosphorus. Aromatic cyclic groups are comprised of at least one aromatic ring. Non-aromatic cyclic groups are comprised of a ring structure with no aromatic rings. The phenyl ring may also be incorporated in multi ring systems examples of which include, but are not limited to, acridine, anthracene, benzazapine, benzodioxepin, benzothiadiazapine, carbazole, cinnoline, fluorescein, isoquinoline, naphthalene, phenanthrene, phenanthradine, phenazine, phthalazine, quinoline, quinoxaline, and other like polycyclic aromatic hydrocarbons. Additional moieties that can be substituted on the phenyl ring include, but are not limited to, mono- or di-substituted amino, unsubstituted amino, ammonium, alkoxy, acetoxy, aryloxy, acetamide, aldehyde, benzyl, cyano, nitro, thio, sulfonic, vinyl, carboxyl, nitroso, trihalosilane, trialkylsilane, trialkylsiloxane, trialkoxysilane, diazeniumdiolate, hydroxyl, halogen, trihalomethyl, ketone, benzyl, and alkylthio.

Molecules according to the present invention may be derived from commercially available benzyl chloride. Alternatively, benzyl chloride may be synthesized in a number of ways, including, but not limited to; photo catalyzed chlorination of toluene, peroxide-catalyzed chlorination of toluene, and chloromethylation of benzene. Additionally, phenyl rings containing more than one chloromethylation site are contemplated.

In one preferred embodiment of the present invention, using Formula 2, a molecule may be synthesized in a two-step procedure as outlined in Scheme 1. In the first step (1), benzyl chloride is treated using methods known in the art to replace the —Cl atom with a nucleophilic substituent. It is desirable that the nucleophilic substituent activates the benzylic carbon protons for the introduction of diazeniumdiolate functional groups. In a preferred embodiment of this invention, the atom replacing the —Cl atom is an electronegative heteroatom. It is preferred that the nucleophilic group replacing the —Cl atom is electron withdrawing. Additional preferred substituents may be selected from a group that includes —OR, —NR$^1$R$^2$, and —SR. The —OR group may be, but is not limited to, —OCH$_3$, —OC$_2$H$_5$, and —OSi(CH$_3$)$_3$. The replacing group may be a thiol group, such as, but not limited to, —SC$_2$H$_5$, and -SPh (substituted or unsubstituted). The replacing group may also be a amine, such as, but not limited to, —N(C$_2$H$_5$)$_2$.

The second step (2) in Scheme 1 requires treatment of the molecule with a base in the presence of NO gas. The solvent for the reaction should not react with NO in the presence of a base as does acetonitrile or ethanol. Suitable solvents for the reaction include, but are not limited to, THF and DMF. Suitable bases include, but are not limited to, sodium methoxide and sodium trimethylsilanolate. In accordance with the method of the invention the resulting molecules derived from benzyl chloride following these procedures will contain multiple —[N(O)NO]$^-$ functional groups which spontaneously release NO in aqueous media. The $R^2$ substituent referred to in the general Formulas and Scheme 1 represents a pharmaceutically acceptable counterion, hydrolysable group, or enzymatically-activated hydrolysable group as described above. $R^4$ may be a proton or a substitution on the phenyl ring or another chloromethylated position.

Scheme 1.

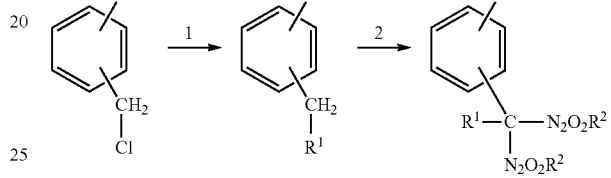

General Chemistry and Strategies to Control Release of NO

Without restraint to any one theory, the importance of the benzylic structure (methylphenyl group) to the invention is threefold. First, the benzylic carbon has relatively acidic protons and the choice of nucleophile should increase the acidity of the benzylic protons such that a base can easily extract a proton. Exposure of benzylic compounds to NO gas in the absence of base is not known to produce the diazeniumdiolate functional group. Secondly, the aromatic ring resonance stabilizes the carbanion formed by extraction of a proton by base. The stabilized carbanion allows for the reaction of the carbanion with NO, to produce a radical carbon center and nitroxyl anion (NO$^-$). Further reaction of the radical carbon center with NO or NO dimer produces the diazeniumdiolate functional group. The anionic diazeniumdiolate functional group enhances the acidity of the remaining benzylic proton(s) and allows an additional diazeniumdiolate group to be added to the carbon. In this manner, up to three diazeniumdiolate functional groups are introduced into the molecule via the benzylic carbon. Thirdly, the presence of resonant electrons in the aromatic ring helps promote spontaneous decomposition of the —[N(O)NO]— group in aqueous media. Other bisdiazeniumdiolates, namely methylene bisdiazeniumdiolate [H$_2$C(N$_2$O$_2$Na)$_2$] lack resonant electronic forces that participate in the decomposition process and thus show remarkable stability (inability to release NO) in solution (Traube, 1898).

Another preferred way of reaching the desired amount and rate of NO release on a macro scale is to blend two or more of the individually synthesized molecules together to achieve the desired rate of NO release from the mixture.

Molecules that release NO can be used to provide localized fluxes of NO at specific target sites. For example, molecules of Formula 1 and 2 can be non-covalently associated with, part of, dispersed within, incorporated with, or contained within a polymer matrix by physical or chemical means. This may be accomplished by mixing a molecule of Formula 1 or 2 into a polymer melt comprised of but not limited to poly(ethylene)glycol, poly(caprolactone), poly(urethane), poly(vinyl chloride), and then casting the polymer into the desired shape, similar to methods described in Mowery et al. (2000). Alternatively, co-precipitation can be done by solubilizing the polymer with the small molecule NO donor and allowing the solvent to evaporate, similar to methods described in U.S. Pat. No. 5,405,919, Keefer et al. Other methods known to one skilled in the art may be used to non-covalently incorporate molecules of the current invention into a polymeric matrix.

In addition to localizing the effects of NO, any means of non-covalently incorporating compounds of the present invention into a polymer matrix allows for ability to remove the incorporated NO donor from solution or suspension by filtration or centrifugation. Non-covalent incorporation within a polymer matrix allows for embodiments of the invention to be used in medical devices such as but not limited to stents, vascular grafts, extracorporeal devices used in surgery, catheters, cannulea, artificial joints and prostheses, and any device that can be implanted on a temporary or permanent basis within or on the body.

Use in Coatings for Medical Devices

In order for NO to be therapeutic it is most preferable that it be delivered/produced at the site of interest. The molecules described herein have the potential to generate a prolonged flux of NO at the desired area of interest. Localization of the NO-releasing molecules of the present invention to a medical device, using non-covalent forms of polymerization including but not limited to: associated with, part of, dispersed within, incorporated with, or contained within a polymer matrix by physical or chemical means and other methods known to those skilled in the art, can provide a localized flux of NO without any deleterious systemic effects such as hypotension. For example, this may be accomplished by mixing a molecule of Formula 1 or 2 into a polymer melt comprised of but not limited to poly(ethylene)glycol, poly(caprolactone), poly(urethane), poly(vinyl chloride), and then casting the polymer into the desired shape, similar to methods described in Mowery et al. (2000). Alternatively, co-precipitation can be done by solubilizing the polymer with the small molecule NO donor and allowing the solvent to evaporate, similar to methods described in U.S. Pat. No. 5,405,919, Keefer et al. Other methods known to one skilled in the art may be used to non-covalently incorporate molecules of the current invention into a polymeric matrix.

Such non-covalent polymerization methods allow for embodiments of the present invention to be used in medical devices such as but not limited to stents, vascular grafts, extracorporeal devices used in surgery, catheters, cannulea, artificial joints and prostheses, and any device that can be implanted on a temporary or permanent basis within or on the body.

Vascular Stents

The current state of the art vascular stents are designed to elute anti-proliferative medications such as sirolimus as a means to inhibit restenosis. However, these drugs are not antithrombotic and patients have developed life threatening blood clots. The sirolimus eluting stent exemplifies a fundamental problem underlying the development of both drug-eluting and non-drug-eluting stents.

Nitric oxide inhibits platelet aggregation (Moncada et al., 1991), prevents smooth muscle cell proliferation (Mooradian et al., 1995) and promotes re-endothelialization of the injured vessel (Ziche et al., 1994). A vascular stent can be coated with the present invention to elute therapeutic amounts of NO which would accelerate the healing process following PTCA stent deployment thus improving patient outcome. over the current state of the art drug eluting stents.

By way of example and not limitation, a cardiovascular stent comprised of or coated with the NO-releasing molecules of the present invention will possess the ability to resist platelet adhesion, prevent platelet aggregation and inhibit vascular smooth muscle cell proliferation (Mooradian et al., 1995). The current state of the art anti-proliferative eluting stents do not inhibit blood clot formation. Patients receiving these stents must maintain a 3-month regimen of anti-clotting medication. Recent reports disclose the detection of blood clots in dozens of patients who have received this type of stent (Neergaard, 2003). One skilled in the art can envision a coating that releases both the anti-proliferative drug and NO simultaneously.

The proliferation of endothelial cells (ECs) mediated by NO is of great interest because EC proliferation is the first step towards neovascularization (Ausprunk, 1977). Compounds of the present invention may be used in non-covalently polymerized forms as described above in order to stimulate EC proliferation onto medical devices such as but not limited to vascular stents or grafts. As the ECs become confluent on the surface of the device, blood contact with the device will be minimize and replaced by a natural cellular layer, thus imparting biocompatibility to the implanted device.

Indwelling Catheters

An endemic problem associated with hospitalization is manifested in the number of infections and deaths directly related to inserted medical devices such as catheters, shunts, and probes. It is estimated that up to 20,000 deaths occur each year due to infection acquired from vascular catheterization. The inserted medical device provides direct access into the body for microorganisms. These bacteria adhere to and colonize upon the inserted device and in the process may form an antibiotic resistant matrix known as a biofilm. As the biofilm grows, planktonic cells can break free and spread the infection further into the patient. Infections can be prevented by killing the bacteria before they can colonize the medical device or by preventing the adhesion of bacteria to the device such that a biofilm cannot form.

Regarding microbial adhesion prevention, a recent report demonstrates that NO can inhibit bacterial adhesion (Nablo et al., 2001). Polyaminosiloxanes were deposited on glass slides and derivatized into NO donors. *P. aeruginosa* adhesion was inhibited in a dose dependent manner by the NO-releasing sol-gels. This early report strongly suggests that bacterial adhesion can be influenced by surfaces designed to release NO. Therefore, catheters comprised of or containing NO-releasing molecules of the present invention may inhibit biofilm formation and improve patient health care.

Compounds of the present invention may be used to reduce or eliminate the microbial adherence and growth on indwelling catheters and other medical devices. One skilled in the art can devise a coating incorporating the compounds of the present invention whereby the quantity of NO released is of sufficient flux and duration to inhibit the adhesion and subsequent growth of microbial contaminants.

Use of the Present Invention as a Pharmaceutical Agent

Because of the multifunctional role of NO in physiology, compounds of Formulas 1 and 2 can have a wide range of utilities in biology and medicine. Embodiments of the present invention may be used to treat but would not be limited to treating cardiovascular disorders including high blood pressure, formation of thrombi and restenosis. The present invention may also be used to treat but is not limited to treating impotence, microbial infections, parasitic infestations, gastric motility disorders including forms of irritable bowel syndrome, cancer, wounds and any disorder where an application of NO would be useful.

A number of suitable routes of administration may be employed for treatment of animals, preferably mammals, and in particular in humans to provide an effective dose of nitric oxide using the current invention. A pharmaceutical composition may be comprised of any diazeniumdiolate in Formulas 1 and 2 for the purposes of oral, inhalation, intranasal, intravenous, subcutaneous, intramuscular, topical, transdermal, and rectal administration. The pharmaceutical composition may include an acceptable pharmaceutical carrier.

While Formula I and II compounds provided herein may be formulated into injectable preparations and oral preparations in ways usual for these routes of administration, and the following methods and excipients are exemplary of usual and acceptable means, they should not be considered to limit the scope of the present invention with respect to pharmaceutical compositions.

The compounds of the present invention may be formulated into preparations for injections by dissolving, suspending, or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives. Parenteral administration of the compounds of the present invention may also be had by a pharmaceutically acceptable carrier such as dextrose, sterile water for injection, USP, or by normal saline.

In the case of oral preparations, the compounds may be used alone or in combination with appropriate additives to make tablets, powders, granules or capsules, e.g., with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

Of the possible solid oral dosage forms, the preferred embodiments include tablets, capsules, troches, cachets, powders, dispersions and the like. Other forms are also possible. Preferred liquid dosage forms include, but are not limited to, non-aqueous suspensions and oil-in-water emulsions.

In one embodiment of a solid oral dosage form, a tablet includes a pharmaceutical composition according to the present invention as the active ingredient, or a pharmaceutically acceptable salt thereof, which may also contain pharmaceutically acceptable carriers, such as starches, sugars, and microcrystalline cellulose, diluents, granulating agents, lubricants, binders, disintegrating agents, and, optionally, other therapeutic ingredients. Because of the instability of the diazeniumdiolates in acid, it is advantageous to coat oral solid dosage forms with an enteric or delayed-release coating to avoid release of the entire dose of nitric oxide in the stomach, unless the stomach is the therapeutic target organ.

A preferred method of coating the solid dosage form includes the use of non-aqueous processes to enteric or time-release coat the dosage form in order to reduce the likelihood that nitric oxide will be released from the dosage form during the coating process. These non-aqueous coating techniques are familiar to one skilled in the art, such as that described in U.S. Pat. No. 6,576,258. A time-release coating has been described in U.S. Pat. No. 5,811,121 that uses a alkaline aqueous solution to coat solid dosage forms. This coating process would also serve to preserve the levels of diazeniumdiolate in the dosage form, as the release rate of nitric oxide from compounds of the present invention is greatly decreased at higher pH levels.

Rectal and additional dosage forms can also be developed by a person skilled in the art, keeping in mind the acid instability of the diazeniumdiolate class of compounds and their sensitivity to aqueous solutions at neutral pH. Intramuscular formulations of the present invention may be formulated in oil or in oil-in-water emulsions.

Due to their chemical structures, the compounds of the present invention wherein $R^2$ is a pharmaceutically acceptable cation are most preferably administered by intravenous injection. Compounds of Formula I and II, wherein $R^2$ is a pharmaceutically acceptable metal center or an organic group are preferably administered either intravenously or orally. The compounds of the present invention are made into pharmaceutical injectable or oral compositions by combination with appropriate pharmaceutically acceptable carriers or diluents. One of ordinary skill in the art would be able to develop appropriate dosage forms on the basis of knowledge with excipients which are suitable for the desired pharmaceutical formulation.

Use in Microbicidal Applications

Compounds of the present invention may be used on inanimate objects to reduce the amount of potentially pathogenic bacteria, fungi, virus, or parasite levels on the surface of the object. This is accomplished by placing the object in contact with a solution of a compound of the present invention that is of sufficient strength, and for a sufficient duration to reduce the amount of potentially pathogenic microbe. "Potentially pathogenic" means that the microbe has the capability of infecting an animal such as a mammal. The microbicidal solution may contain a variety of other ingredients that may or may not be involved in killing microbes.

Use in Platelet Storage Applications

One non-limiting example of the utility of NO-releasing molecules is in the ex vivo inhibition of platelets. Nitric oxide has been shown to be a potent inhibitor of platelet aggregation (Moncada et al., 1991). Application of NO to platelets also results in a decreased intracellular calcium response to agonists (Raulli, 1998) as well as other intracellular processes dependent on calcium, such as release of granule contents (Barrett et al., 1989).

This ability of NO-releasing molecules to inhibit platelet activation ex vivo may be of considerable utility in the treatment of Platelet Storage Lesion (PSL). Platelet Storage Lesion is defined as the sum of the changes that occur in platelets following their collection, preparation, and storage (Chrenoff, 1992), and is responsible for the loss of platelet functionality that increases with increased duration of storage.

One skilled in the art can devise a number of ways to treat stored platelets with NO-releasing molecules. An exemplary embodiment of the present invention uses a compound of the present invention that is manufactured pre-loaded within the blood storage compartment. The molecule should be of appropriate quantity and release rate to partially or completely inhibit platelet activation for a specified amount of platelet-rich plasma (PRP), platelet concentrate (PC), apheresed platelets (APP), or other platelet product that would be traditionally stored. The molecule should release inhibitory levels of nitric oxide for sufficient duration to cover the entire predicted duration period for the platelet product, although paradigms can be envisioned where the inhibitory flux of nitric oxide need not be present for the entire duration of storage.

The NO-releasing compound of the present invention may be a single entity or a blend of molecules designed to reach an optimized release rate and duration of NO release. One skilled in the art would appreciate that the compounds of the present invention could be part of a complete manufactured system for platelet storage as described in U.S. Provisional Patent Application No. 60/471,724 filed May 20, 2003 by Raulli et al., and entitled Systems and Methods for Pathogen Reduction in Blood Products.

Use in Pathogen Reduction of Stored Human Platelets

It has been well established that nitric oxide can kill a variety of bacterial, fungal and viral pathogens (DeGroote and Fang, 1995). An exemplary embodiment of the current invention uses a nitric oxide-releasing molecule within the blood storage compartment that delivers sufficient levels of nitric oxide to reduce or eliminate viable microbes that may be contaminating the blood product.

The molecule of the present invention will release sufficient levels of nitric oxide at an appropriate rate and for sufficient duration to kill, inactivate, or retard the further growth of pathogens that contaminate the blood product. Further, the molecule is compatible with blood cells and blood plasma. One skilled in the art would appreciate that the compounds of the present invention could be part of a complete manufactured system for platelet storage as described in U.S. Provisional Patent Application No. 60/471,724 filed May 20, 2003 by Raulli et al., and entitled Systems and Methods for Pathogen Reduction in Blood Products.

Use in the Generation of Nitric Oxide Gas

Compounds of the present invention may be used to generate nitric oxide gas without the formation of carcinogenic nitrosamines. Nitric oxide gas may be used combined with air, oxygen and other gasses to treat pulmonary hypertension. Nitric oxide gas may be generated within a compartment that is comprised of a gas permeable membrane as disclosed in U.S. Provisional Patent Application No. 60/471,724, whereby the NO gas is transferred to a separate compartment through the gas permeable membrane.

In general, it is useful to begin the generation of NO in a container where the air or any gas comprised of oxygen in whole or in part has been evacuated. This will minimize the production of $NO_2$ from the reaction of NO with oxygen. Compounds of the present invention are placed in the chamber where NO is to be generated and the chamber is evacuated. If the gas is to be generated rapidly, an appropriate amount of acidic solution is added to the chamber in a manner that retains the integrity of the vacuum in the chamber. The chamber should be of sufficient size to contain the generated gas without creating high pressures. The appropriate amount of compound of the present invention can be matched with the volume of the container by using the Ideal Gas Law. Should high pressure be desired, the chamber should be comprised of materials to withstand such pressures. The compounds of the present invention may also be activated to release NO using water if they are combined with a sufficient quantity of an acid in powdered form. Applications can be envisioned where it may be useful to have the NO mixed with air. In this case, the desired volume of air can be added to the chamber before or after generation of NO. One skilled in the art would also appreciate that the compounds of the present invention could be part of a complete manufactured system for sterilization as described in U.S. Provisional Patent Application Nos. 60/534,395; 60/575,421; and 60/564,589, each of which is hereby incorporated by reference in its entirety.

In another embodiment of the present invention, NO may be generated by mixing the NO donor with a photoacid. Illumination produces the acid which serves to activate NO release. Suitable photoacid generators include, but are not limited to, triphenylsulfonium triflate, 2-naphthyl diphenyl-sulfonium triflate, 2-(4-methoxystyryl)-4,6-bis(trichloromethyl)-1,3,5-triazine, and diphenyliodonium hexafluorophosphate.

EXAMPLES

The following examples further illustrate the present invention. Except where noted, all reagents and solvents are obtained from Aldrich Chemical Company (Milwaukee, Wis.). Nitric Oxide gas is supplied by Matheson Gas Products. A detailed description of the apparatus and techniques used to perform the reactions under an atmosphere of NO gas has been published (Hrabie et al., 1993) and is incorporated herein by reference in its entirety. The IR spectra are obtained on a Perkin Elmer 1600 series FTIR. Monitoring and quantification of the evolved NO gas is performed using a Thermo Environmental Instruments Model 42C NO—$NO_2$—NOx detector calibrated daily with a certified NO gas standard. The quantity of NO released is measured in parts per billion ppb, which is determined as follows: the NO-releasing material is placed in a chamber that has a steady stream on nitrogen gas flowing through it. The nitrogen is a carrier gas that serves to sweep any NO that is generated within the chamber into a detector. A measurement of 100 ppb means that 100 molecules of NO was generated for every billion of the nitrogen gas sweeping the chamber.

Example 1

This example converts a benzyl ether into an NO-releasing agent.

Commercially available from Sigma-Aldrich is benzyl methyl ether, $PhCH_2OCH_3$. To 100 ml of diethyl ether in a Parr pressure vessel, 3.62 g (0.032 moles) of potassium t-butoxide is added with stirring. To this suspension 2 ml (0.016 moles) of benzyl methyl ether is slowly added. Oxygen is removed from the flask by alternating cycles (10) of inert gas pressurization and venting. The stirred solution is then exposed to 80 psi NO gas at room temperature for 24 hours. When the reaction is complete, i.e. no more NO gas was consumed, then the head space is purged of NO gas and the tan solid filtered and washed with ether. The UV-vis spectrum of this material has a peak at 258 nm and it yields a positive Greiss reaction. The crude tan product is analyzed for NO release. A solution is made of 6.7 mg of the tan product in 0.1 ml of 10 mM NaOH. In a reactor vessel containing 3 ml of pH 7.4 buffer is injected the 0.1 ml of the tan product solution. The tan product generates 0.13 mg of NO over a 79 minute time period.

Example 2

This example describes methods to convert a benzyl-NR molecule into a carbon-based diazeniumdiolate.

In a Parr pressure vessel, 2.0 g (0.010 moles) of commercially available trimethylammoniumbenzyl chloride is added to 200 ml of t-butanol. With stirring, 3.62 g (0.032 moles) of potassium t-butoxide is slowly added. The head space is flushed with an inert gas before exposure to 60 psi NO gas. The reaction is allowed to proceed at room temperature for 24 hours or until no further consumption of NO gas is observed. The resulting diazeniumdiolate salt is filtered, washed with t-butanol and diethyl ether, and vacuum dried before analysis.

Example 3

This example describes methods to convert a benzyl-SR molecule into a carbon based diazeniumdiolate.

Commercially available benzyl chloride and sodium ethanethiolate are subjected to a nucleophilic substitution reaction to produce $PhCH_2SC_2H_5$ after isolation and purification. In a Parr pressure vessel, 2.0 g (0.013 moles) of $PhCH_2SC_2H_5$ is added to 200 ml of t-butanol. With stirring, 2.94 g (0.026 moles) of potassium t-butoxide is slowly added. The head space is flushed with an inert gas before exposure to 60 psi NO gas. The reaction is allowed to proceed at room temperature for 24 hours or until no further consumption of NO gas is observed. The resulting diazeniumdiolate salt is filtered, washed with t-butanol and diethyl ether, and vacuum dried before analysis.

Example 4

This example describes a method to convert deoxybenzoin into an NO-releasing agent. Commercially available from Sigma-Aldrich is deoxybenzoin, $PhCH_2C(O)$ Ph. Deoxybenzoin, 5.05 g (0.026 moles), is added to 10 ml of THF in a 200 ml beaker. To 15 ml of THF in a 200 ml beaker, sodium trimethylsilanolate 5.96 g (0.053 moles) is added. The deoxybenzoin solution is mixed with the sodium trimethylsilanolate solution in a 300 ml Parr pressure vessel. Oxygen is removed from the flask by alternating cycles (10) of inert gas pressurization and venting. The stirred solution is then exposed to 80 psi NO gas at room temperature for 24 hours. When the reaction was complete, i.e. no more NO gas was consumed, the head space was purged of NO gas and the tan solid product is filtered and washed with ether. The weight of the dried product is 7.78 g. The UV-vis spectrum of this material has a peak at 253 nm (10 mM NaOH), and it yields a positive Greiss reaction. The carbonyl peak is shifted to $1686^{-1}$ cm in the FT-IR (KBr pellet). The tan product can be recrystallized from a methanol/ether solution. The product is analyzed for NO release using chemiluminescence. A stock solution is made consisting of 11.5 mg of the recrystallized product in 50 ml of 10 mM NaOH. In a chemiluminescence reactor vessel containing 3.0 ml of pH 7.4 buffer, 2.0 ml of the product solution is injected. It is observed that over a 275 minute time period 0.0093 mg of NO is produced. This corresponds to 0.020 mg of NO per mg of compound.

Example 5

This example describes a method to convert 1,3-diphenylacetone into an NO-releasing agent. Commercially available from Sigma-Aldrich is 1,3-diphenylacetone, $PhCH_2C(O)CH_2Ph$. Diphenylacetone (2.14 g, 0.010 mol) is added to a 300 ml Parr pressure vessel. Sodium trimethylsilanolate (4.28 g, 0.038 mol) is added to 40 ml of THF in a 200 ml beaker. The sodium trimethylsilanolate solution is then added to 1,3-diphenylacetone in the Parr pressure vessel with stirring. Oxygen is removed from the flask by alternating cycles (10) of inert gas pressurization and venting. The stirred solution is then exposed to 80 psi NO gas at room temperature for 24 hours. When the reaction is complete, i.e. no more NO gas was consumed, the head space is purged of NO gas and the tan solid product is filtered and washed with ether. The weight of the dried product is 5.9 g. The UV-vis spectrum of this material has a peak at 257.4 nm (10 mM NaOH) and it yields a positive Greiss reaction. Upon addition of acid to the sample, the 257.4 nm peak shifts to 243 nm. A carbonyl peak at $1714^{-1}$ cm is observed in the FT-IR (KBr pellet). The recrystallized white product is analyzed for NO release. A stock solution is made of 38.9 mg of the recrystallized white product in 50 ml of 10 mM NaOH. In a chemiluminescence reactor vessel containing 3.0 ml of pH 7.4 buffer, 1.0 ml of the product solution is injected. It is observed over a 331 minute time period that 0.0105 mg of NO is produced. This corresponds to 0.013 mg NO per mg compound.

Example 6

This example shows the use of the present invention as a microbicide against exemplary pathogen S. epidermides.

An inanimate object, such as a surgical tool or medical device, is deliberately contaminated with S. epidermides and submerged in a buffered solution of a compound of the present invention at a concentration range between 2 mg/ml to the limit of saturation, and at a duration ranging from 5 min to 48 hours. A similar inanimate object also contaminated with an identical amount of S. epidermides is submerged in a buffered solution that does not contain a compound of the present invention for the identical time period. After varying time periods, each of the inanimate objects is rinsed and submerged in separate flasks containing a sterile broth that supports the growth of S. epidermides, and the broths are incubated for 24 hours at 37° C. with vigorous back and forth shaking. The growth of S. epidermides in the flask is measured for both the object exposed to a compound of the present invention, and the object not exposed, and the measurements are compared.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed:

1. A composition comprising a C-based diazeniumdiolate compound of the formula:

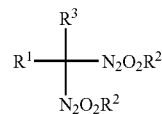

wherein $R^1$ is selected from the group consisting of an electron withdrawing group, a nitro group, an ether, a thioether, and a non-enamine amine;

wherein $R^2$ is selected from the group consisting of a countercation and a protecting group on the terminal oxygen; and wherein $R^3$ is a substituted phenyl wherein a substituent substituted on said substituent is selected from the group consisting of mono- or di-substituted amino, unsubstituted amino, ammonium, alkoxy, acetoxy, aryloxy, acetamide, aldehyde, benzyl, cyano, nitro, sulfo, vinyl, carboxyl, nitroso, trihalosilane, trialkylsilane, trialkylsiloxane, trialkoxysilane, diazeniumdiolate, hydroxyl, halogen, trihalomethyl, benzyl, and alkylthio, wherein said substituted phenyl may be incorporated in a multi-ring system.

2. The composition of claim 1, wherein the $R^3$ phenyl is incorporated in a multi-ring system.

3. The composition of claim 2, wherein the multi-ring system is selected from the group consisting of acridine, anthracene, benzazapine, benzodioxepin, benzothiadiazapine, carbazole, cinnoline, fluorescein, isoquinoline, naphthalene, phenanthrene, phenanthradine, phenazine, phthalazine, quinoline, and quinoxaline.

4. The composition of claim 1, wherein $R^2$ is a protecting group selected from the group consisting of aryl, glycosyl, acyl, alkyl and olefinic groups.

5. The composition of claim 1, wherein $R^2$ is a protecting group selected from the group consisting of aryl, glycosyl, acyl, alkyl and olefinic groups, and wherein said aryl group is 2,4-dinitrophenyl.

6. The composition of claim 1, wherein $R^2$ is a protecting group selected from the group consisting of aryl, glycosyl, acyl, alkyl and olefinic groups, and wherein said alkyl group is selected from the group consisting of saturated alkyl, unsaturated alkyl, straight-chain alkyl, branched-chain alkyl, and substituted or unsubstituted alkyl.

7. The composition of claim 1, wherein $R^2$ is a protecting group selected from the group consisting of aryl, glycosyl, acyl, alkyl and olefinic groups, and wherein said alkyl group is selected from the group consisting of saturated alkyl, unsaturated alkyl, and functionalized alkyl, and wherein said functionalized alkyl is selected from the group consisting of 2-bromoethyl, 2-hydroxypropyl, 2-hydroxyethyl and S-acetyl-2mercaptoethyl.

8. The composition of claim 1, wherein $R^2$ is a protecting group selected from the group consisting of aryl, glycosyl, acyl, alkyl and olefinic groups, and wherein said olefinic group is a vinyl group.

* * * * *